United States Patent
Liu et al.

(10) Patent No.: US 8,357,674 B2
(45) Date of Patent: *Jan. 22, 2013

(54) ANALOGUES OF CILOSTAZOL

(75) Inventors: Julie F. Liu, Lexington, MA (US); Rose A. Persichetti, Stow, MA (US)

(73) Assignee: CoNCERT Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/538,952

(22) Filed: Jun. 29, 2012

(65) Prior Publication Data

US 2012/0264721 A1 Oct. 18, 2012

Related U.S. Application Data

(63) Continuation of application No. 12/150,107, filed on Apr. 24, 2008, now abandoned.

(60) Provisional application No. 60/926,100, filed on Apr. 25, 2007.

(51) Int. Cl.
| | |
|---|---|
| *A61K 31/4709* | (2006.01) |
| *A61K 31/616* | (2006.01) |
| *A61P 3/10* | (2006.01) |
| *A61P 9/00* | (2006.01) |
| *A61P 3/04* | (2006.01) |
| *A61P 7/02* | (2006.01) |
| *A61P 1/04* | (2006.01) |
| *A61P 11/06* | (2006.01) |
| *A61P 15/00* | (2006.01) |
| *A61P 9/10* | (2006.01) |
| *C07D 401/12* | (2006.01) |

(52) U.S. Cl. ......... 514/161; 514/312; 514/301; 546/158
(58) Field of Classification Search .................. None
See application file for complete search history.

(56) References Cited

U.S. PATENT DOCUMENTS

| | | | |
|---|---|---|---|
| 4,277,479 | A | 7/1981 | Nishi et al. |
| 6,221,335 | B1 | 4/2001 | Foster |
| 6,440,710 | B1 | 8/2002 | Keinan et al. |
| 6,603,008 | B1 | 8/2003 | Ando et al. |
| 7,517,990 | B2 | 4/2009 | Ito et al. |
| 2007/0082929 | A1 | 4/2007 | Gant et al. |
| 2007/0197695 | A1 | 8/2007 | Potyen et al. |
| 2008/0103122 | A1 | 5/2008 | Veltri |

FOREIGN PATENT DOCUMENTS

| | | |
|---|---|---|
| WO | WO-9526325 A2 | 10/1995 |
| WO | WO-2007/118651 A1 | 10/2007 |
| WO | WO-2008/133949 A1 | 11/2008 |

OTHER PUBLICATIONS

Baillie, Thomas A., "The Use of Stable Isotopes in Pharmacological Research," *Pharmacological Reviews*, vol. 33, No. 2, p. 81-132.1981.

Browne, Thomas R., "Stable Isotope Techniques in Early Drug Development: An Economic Evaluation," *J. Clin. Pharmacol.*, vol. 38, pp. 213-220, 1998.

Cherrah, et al., "Study of Deuterium Isotope Effects on Protein Binding by Gas Chromatography/Mass Spectrometry Caffeine and Deuterated Isotopomers," *Biological and Environmental Mass Spectrometry*, vol. 14, pp. 653-657, 1998.

Dyck, et al., "Effects of Deuterium Substitution on the Catabolism of β-Phenylethylamine: An In Vivo Study," *Journal of Neurochemistry*, vol. 46, No. 2, pp. 399-404, 1986.

Fisher, et al., "The complexities inherent in attempts to decrease drug clearance by blocking sites of CYP-mediated metabolism," *Current Opinion in Drug Discovery Development*, vol. 9, No. 1, pp. 101-109, 2006.

Food and Drug Administration's Guidance for Industry, Sterile Drug Products Produced by Aseptic Processing—Current Good Manufacturing Practice (Sep. 2004).

Foster, Allan B., "Deuterium isotope effects in the metabolism of drugs and xenobiotics," *Advances in Drug Resrearch*, vol. 14, pp. 2-40, 1985.

Foster, Allan B., "Deuterium isotope effects in studies of drug metabolism," *TIPS*, pp. 524-527, Dec. 1984.

Gouyette, et al., "Synthesis of Deuterium-labelled Elliptinium and its Use in Metabolic Studies," *Biomedical and Environmental Mass Spectrometry*, vol. 15, pp. 243-247, 1988.

Haskins, N. J., "The Application of Stable Isotopes in Biomedical Research," *Biomedical Mass Spectrometry*, vol. 9, No. 7, pp. 269-277, 1982.

Honma, et al., "Liberation of Deuterium from the Piperidine Ring During Hydroxylation," *Drug Metabolish and Disposition*, vol. 15, No. 4, pp. 551-559, 1999.

Kushner et al., "Pharmacological Uses and Perspectives of Heavy Water and Deuterated Compounds," *Can. J .Physiol. Pharmacol.*, vol. 77, pp. 79-88, 1999.

Mallikaarjun et al., Interaction Potential and Tolerability of the Coadministration of Cilostazol and Aspirin, 37 (Suppl. 2) Clin. Pharmacokinet 87-93 (1999).

Physicians' Desk Reference® product label and information for PLETAL®, *Physicians' Desk Reference*, Edition 63, 2009, pp. 2481-2484.

(Continued)

*Primary Examiner* — Janet Andres
*Assistant Examiner* — Timothy R Rozof
(74) *Attorney, Agent, or Firm* — Kenyon & Kenyon LLP

(57) ABSTRACT

This invention relates to novel compounds which are derivatives of the phosphodiesterase inhibitor, cilostazol and pharmaceutically acceptable salts thereof. This invention also provides pyrogen-free compositions comprising one or more compounds of the invention and the use of the disclosed compounds and compositions in methods of treating diseases and conditions that are treated by administration of an phosphodiesterase inhibitor, such as cilostazol. The invention also relates to the use of the disclosed compounds and compositions as reagents in analytical studies involving cilostazol.

14 Claims, No Drawings

OTHER PUBLICATIONS

Pieniaszek, et al., "Moricizine Bioavailability via Simultaneous, Dual, Stable Isotope Administration: Bioequivalence Implications," *The Journal of Clinical Pharmacology*, vol. 39, pp. 817-825, 1999.

Tonn et al., "Simultaneous Analysis of Diphenhydramine and a Stable Isotope Analog ($^2H_{10}$) Diphenhydramine Using Capillary Gas Chromatography with Mass Selective Detection in Bilogical Fluids from Chronically Instrumented Pregnant Ewes," Biological Mass Spectrometry, vol. 22, pp. 633-642, 1993.

Wolen, Robert L., "The Application of Stable Isotopes to Studies of Drug Bioavailability and Bioequivalence," *The Journal of Clinical Pharmacology*, vol. 26, pp. 419-424, 1986.

PCT International Search Report for International Application No. PCT/US2008/005301, Aug. 26, 2008.

PCT Written Opinion of the International Searching Authority for International Application No. PCT/US2008/005301, Aug. 16, 2008.

Liu et al., "Deuterium in Drugs for Cardiovascular Disease: Design and Synthesis of Deuterated Cilostazol and Ranolazine Analogs with Enhanced Metabolic Stability," Concert Pharmaceuticals, Inc., Lexington, MA, 2010, 1 page.

ANALOGUES OF CILOSTAZOL

RELATED APPLICATION

This application is a continuation of U.S. patent application Ser. No. 12/150,107, filed Apr. 24, 2008, and claims the benefit of U.S. Provisional Application No. 60/926,100, filed on Apr. 25, 2007.

The entire teachings of the above application(s) are incorporated herein by reference.

BACKGROUND OF THE INVENTION

Cilostazol is known by the chemical name 6-[4-(1-Cyclohexyl-1H-tetrazol-5-yl)butoxy]-3,4-dihydro-2(1H)-quinolinone. It is marketed under the tradename PLETAL® (Otsuka America Pharmaceutical, Inc.) in the United States for the treatment of intermittent claudication and under the tradename PLETAL® in Japan and South Korea for the treatment of chronic arterial occlusive disease, including diabetic complications of the peripheral vasculature. Cilostazol is also approved in Europe. The recommended daily dose is 100 mg BID, with 50 mg BID recommended if co-administering strong inhibitors of CYP3A4 and CYP2C19.

Cilostazol is a selective inhibitor of phosphodiesterase III with antiplatelet and antithrombotic activity. More specifically, cilostazol and several of its metabolites are cyclic AMP (cAMP) phosphodiesterase III inhibitors (PDE III inhibitors), inhibiting phosphodiesterase activity and suppressing cAMP degradation. This action results in an increase in cAMP in platelets and blood vessels, leading to inhibition of platelet aggregation and vasodilation, respectively. For example, cilostazol reversibly inhibits platelet aggregation induced by a variety of stimuli, including thrombin, ADP, collagen, arachidonic acid, epinephrine, and shear stress.

Currently, there are fifteen ongoing clinical trials for cilostazol in the areas of cerebral infarction, cerebrovascular disorders, atherosclerosis, diabetes mellitus complications, peripheral vascular disease, Reynaud's disease, intermittent claudication, ischemic heart disease, and acute coronary syndrome.

Additional trials are investigating cilostazol in combination with other therapeutics. For example, trials are investigating cilostazol in combination with aspirin in ischemic stroke patients ("Overcome Biochemical Aspirin Resistane [sic] Through Cilostazol Combination (ARCC)") and in combination with aspirin in chronic stroke patients studying the effect of aspirin plus cilostazol and aspirin alone on the progression of intracranial arterial stenosis, in 200 chronic stroke patients with 50-99% stenosis.

Despite the beneficial activities of cilostazol, there is a continuing need for new compounds to treat the aforementioned diseases and conditions.

SUMMARY OF THE INVENTION

This invention relates to novel compounds which are derivatives of the phosphodiesterase inhibitor, cilostazol and pharmaceutically acceptable salts thereof. This invention also provides pyrogen-free compositions comprising one or more compounds of the invention and the use of the disclosed compounds and compositions in methods of treating diseases and conditions that are treated by administration of an phosphodiesterase inhibitor, such as cilostazol. The invention also relates to the use of the disclosed compounds and compositions as reagents in analytical studies involving cilostazol.

DETAILED DESCRIPTION OF THE INVENTION

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

By "disease" is meant any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of cilostazol will inherently contain small amounts of deuterated isotopologues. The concentration of such naturally abundant stable hydrogen and carbon isotopes, notwithstanding this variation, is small and immaterial as compared to the degree of stable isotopic substitution of compounds of this invention. See, for instance, Wada, E., et al., *Seikagaku*, 66: 15 (1994); Ganes, L. Z., et al., *Comp. Biochem. Physiol A Mol. Integr. Physiol.*, 119: 725 (1998).

The compounds of the present invention are distinguished from such naturally occurring minor forms in that the term "compound" as used in this invention refers to a composition of matter that has a minimum isotopic enrichment factor of at least 500 (7.5% deuterium incorporation) for each deuterium atom that is present at a site designated as a site of deuteration in Formula (I).

In the compounds of the invention any atom not specifically designated as a particular isotope is meant to represent any stable isotope of that atom unless otherwise stated. Unless otherwise stated, when a position is designated specifically as "H" or "hydrogen," the position is understood to have hydrogen at its natural abundance isotopic composition.

The term "isotopic enrichment factor" as used herein means the ratio between the isotopic abundance at a specified position in a compound of this invention and the naturally occurring abundance of that isotope. The natural abundance of deuterium is 0.015%.

In other embodiments, a compound of this invention has an isotopic enrichment factor for each deuterium present at a site designated as a potential site of deuteration on the compound of at least 1000 (15% deuterium incorporation), at least 1500 (22.5% deuterium incorporation), at least 2000 (30% deuterium incorporation), at least 2500 (37.5% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

It is understood that the isotopic enrichment factor of each deuterium present at a site designated as a site of deuteration is independent of other deuterated sites. For example, if there are two sites of deuteration on a compound one site could be deuterated at 22.5% while the other could be deuterated at 37.5% and still be considered a compound wherein the isotopic enrichment factor is at least 1500 (22.5%).

The structural formula depicted herein may or may not indicate whether atoms at certain positions are isotopically enriched. In a most general embodiment, when a structural formula is silent with respect to whether a particular position is isotopically enriched, it is to be understood that the stable isotopes at the particular position are present at natural abundance, or, alternatively, that that particular position is isotopically enriched with one or more naturally occurring stable isotopes. In a more specific embodiment, the stable isotopes are present at natural abundance at all positions in a compound not specifically designated as being isotopically enriched.

The term "isotopologue" refers to a species that differs from a specific compound of this invention only in the isotopic composition thereof or of its ions. Isotopologues can differ in the level of isotopic enrichment at one or more positions and/or in the position(s) of isotopic enrichment.

The term "compound," as used herein, is also intended to include any salts, solvates, or hydrates thereof. Thus, it is to be understood that when any compound is referred to herein by name and structure, salts, solvates, and hydrates thereof are included.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The disclosed compounds may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms.

When the stereochemistry of the disclosed compounds is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% optically pure. Percent optical purity by weight is the ratio of the weight of the enantiomer over the weight of the enantiomer plus the weight of its optical isomer.

When a disclosed compound is named or depicted by structure without indicating the stereochemistry, and has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

"tert" refers to tertiary.

"US" refers to the United States of America.

"FDA" refers to Food and Drug Administration.

"NDA" refers to New Drug Application.

As used herein, "each Y" variable includes, independently, any "Y" group (e.g., Y¹, Y², Y³, and Y⁴).

The term "perdeutero-cyclohexyl" refers to a cyclohexyl group where all the hydrogen are replaced with deuterium.

Therapeutic Compounds

The present invention provides compounds represented by Formula (I):

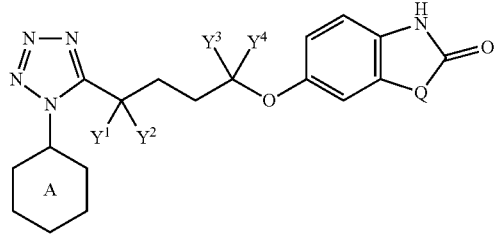

I or a pharmaceutically acceptable salt thereof.

Ring A is a cyclohexyl ring having 0-11 deuterium. Q is —CH₂CH₂— or —CH═CH— where one or more of the hydrogen in Q is optionally replaced by deuterium. Each Y variable is independently selected from hydrogen or deuterium; and at least one Y variable is deuterium or there is at least one deuterium substituent in Q or Ring A, with the proviso that if the only sites of deuteration are on Ring A, Ring A is not a 2,2,6,6, tetradeuterocyclohexyl group. A tetradeutero-cycloheyl group is represented by the following structure:

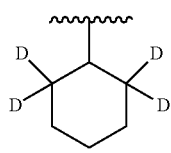

In one embodiment, Y¹ and Y² are the same and Y³ and Y⁴ are the same. In one embodiment, Y¹ and Y² are simultaneously deuterium or Y³ and Y⁴ are simultaneously deuterium. In a particular embodiment, Y¹ and Y² are simultaneously deuterium and Y³ and Y⁴ are simultaneously hydrogen. In another embodiment Y¹ and Y² are simultaneously hydrogen and Y³ and Y⁴ are simultaneously deuterium. In a more particular embodiment, each Y variable is deuterium. In another particular embodiment each Y variable is hydrogen.

In another embodiment, Ring A is:

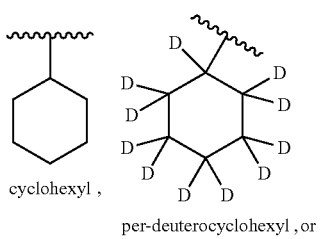

cyclohexyl, per-deuterocyclohexyl, or

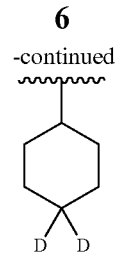

4,4-dideutero-cyclohexyl.

In another embodiment, Q is —CH₂CH₂—, —CD₂CD₂-, —CH═CH—, or —CD═CD-.

In a particular embodiment, Ring A is per-deuterocyclohexyl or 4,4-dideutero-cyclohexyl, each Y is hydrogen and Q is —CH₂CH₂— or —CH═CH—.

In a particular embodiment, Ring A is natural abundance cyclohexyl and each Y variable is hydrogen.

In a particular embodiment, Ring A is 4,4-dideuterocyclohexyl and each Y variable is hydrogen. In another embodiment, Ring A is 4,4-dideuterocyclohexyl, each Y variable is hydrogen, and Q is —CH₂CH₂— or —CH═CH—. In a further embodiment, Ring A is 4,4-dideuterocyclohexyl, each Y variable is hydrogen, and Q is —CD₂CH₂— or —CD₂CD₂-. In still another embodiment, Ring A is 4,4-dideuterocyclohexyl, each Y variable is hydrogen, and Q is —CD₂CD₂-. In yet another embodiment, Ring A is 4,4-dideuterocyclohexyl, Y¹ and Y² are simultaneously deuterium, and Q is —CD₂CD₂-. In still another embodiment, Ring A is 4,4-dideuterocyclohexyl, Y³ and Y⁴ are simultaneously deuterium, and Q is —CD₂CD₂-. In one embodiment, Ring A is 4,4-dideuterocyclohexyl, each Y variable is deuterium, and Q is —CD₂CD₂-.

In another particular embodiment, Ring A is perdeuterocyclohexyl, and each Y variable is hydrogen.

In a particular embodiment, Ring A is perdeutero-cyclohexyl, each Y variable is hydrogen, and Q is —CH₂CH₂— or —CH═CH—. In another embodiment, Ring A is perdeutero-cyclohexyl, each Y variable is hydrogen, and Q is —CD₂CH₂— or —CD₂CD₂-. In yet another embodiment, Ring A is perdeutero-cyclohexyl, each Y variable is hydrogen, and Q is —CD₂CD₂-.

In a particular embodiment, Ring A is perdeutero-cyclohexyl, Y¹ and Y² are simultaneously deuterium, and Q is —CD₂CD₂-. In another embodiment, Ring A is perdeuterocyclohexyl, Y³ and Y⁴ are simultaneously deuterium, and Q is —CD₂CD₂-.

In yet another embodiment, Ring A is perdeutero-cyclohexyl, each Y variable is deuterium, and Q is —CD₂CD₂-.

In yet another embodiment, the invention includes compounds having a combination of Ring "A" and Q selected from the group consisting of: per-deuterocyclohexyl and —CD₂CD₂-; 4,4-dideuterocyclohexyl and —CD₂CD₂-; cyclohexyl and —CD₂CD₂-; per-deuterocyclohexyl and —CD₂CH₂—; 4,4-dideuterocyclohexyl and —CD₂CH₂—; cyclohexyl and —CD₂CH₂—; per-deuterocyclohexyl and —CH₂CH₂—; 4,4-dideuterocyclohexyl and —CH₂CH₂—; per-deuterocyclohexyl and —CD═CD-; 4,4-dideuterocyclohexyl and —CD═CD-; per-deuterocyclohexyl and —CH═CH—; and 4,4-dideuterocyclohexyl and —CH═CH—.

In yet another embodiment, the compound is a compound of Formula I selected from any one of the compounds set forth in Table 1, wherein each Y is hydrogen.

TABLE 1

| Compound | Ring "A" | Q |
|---|---|---|
| 100 | per-deuterocyclohexyl | —CD$_2$CD$_2$- |
| 101 | 4,4-dideuterocyclohexyl | —CD$_2$CD$_2$- |
| 102 | cyclohexyl | —CD$_2$CD$_2$- |
| 103 | per-deuterocyclohexyl | —CD$_2$CH$_2$— |
| 104 | 4,4-dideuterocyclohexyl | —CD$_2$CH$_2$— |
| 105 | cyclohexyl | —CD$_2$CH$_2$— |
| 106 | per-deuterocyclohexyl | —CH$_2$CH$_2$— |
| 107 | 4,4-dideuterocyclohexyl | —CH$_2$CH$_2$— |
| 108 | per-deuterocyclohexyl | —CD=CD- |
| 109 | 4,4-dideuterocyclohexyl | —CD=CD- |
| 110 | per-deuterocyclohexyl | —CH=CH— |
| 111 | 4,4-dideuterocyclohexyl | —CH=CH— |

In an even more specific embodiment, the compound is selected from:

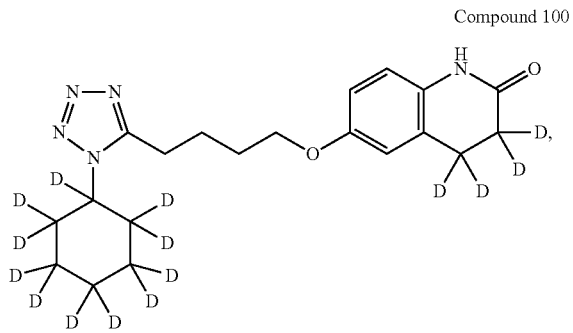

Compound 100

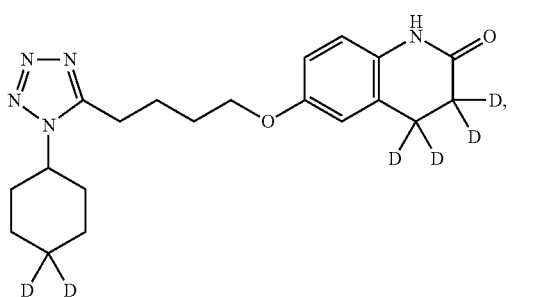

Compound 101

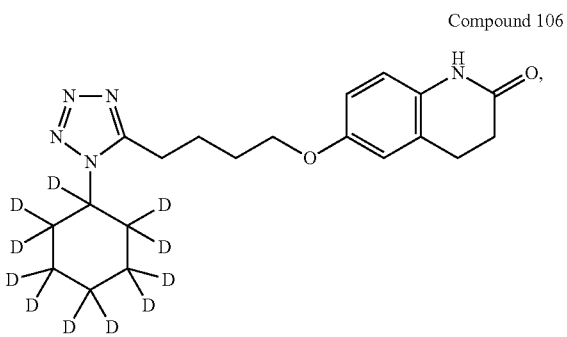

Compound 106

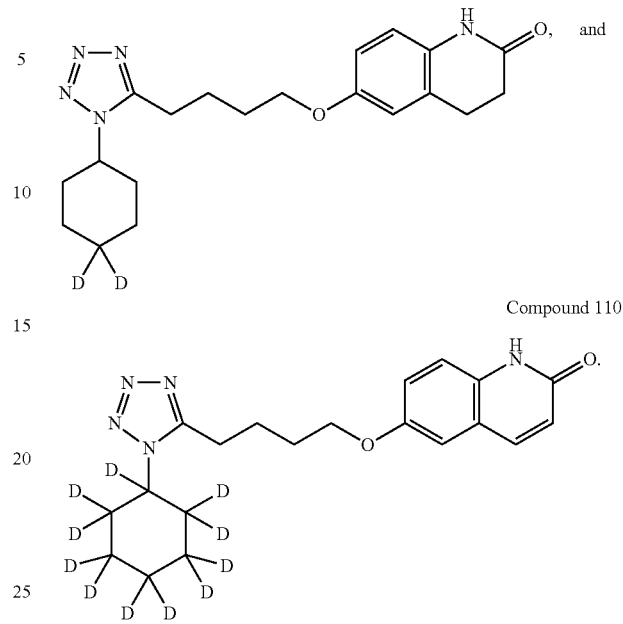

Compound 107, and

Compound 110.

In another set of embodiments, any atom not designated as deuterium in any of the embodiments set forth above is present at its natural isotopic abundance.

Compositions

In another embodiment, the invention also provides pyrogen-free compositions comprising an effective amount of a compound of Formula (I) (e.g., including any of the formulae herein), or a pharmaceutically acceptable salt thereof and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, *Remington's Pharmaceutical Sciences*, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Pharmaceutical compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Pharmaceutical compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, TWEEN 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz, J. D. and Zaffaroni, A. C., U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the patient compositions at the site of interest, such as injection, use of catheters, trocars, projectiles, pluronic gel, stents, sustained drug release polymers or other device which provides for internal access.

Thus, according to yet another embodiment, the compounds and compositions of this invention may be incorporated into coating compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting the device with the coating composition described above. It will be obvious to those skilled in the art that the coating of the device will occur prior to implantation into a mammal.

According to another embodiment, the invention provides a method of impregnating an implantable drug release device comprising the step of contacting the drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that the compound is therapeutically active.

According to another embodiment, the invention provides an implantable drug release device impregnated with or containing a compound or a composition comprising a compound of this invention, such that the compound is released from the device and is therapeutically active.

Where an organ or tissue is accessible because of surgery, such organ or tissue may be bathed in a medium containing a composition of this invention, a composition of this invention may be painted onto the organ, or a composition of this invention may be applied in any other convenient way.

Examples for formulations and compositions relating to the compounds of this invention are described in U.S. Pat. Nos. 7,144,585, 6,923,988 and 6,720,001.

In another embodiment, a pharmaceutical composition of this invention further comprises one or more second therapeutic agents. In one embodiment, the second therapeutic agent is one or more additional compounds of the present invention. In one embodiment, each of the two or more compounds of the invention present in such compositions differs from all others in the positions(s) of isotopic enrichment. Commonly, such a composition comprises three, four, five or more different compounds of this invention.

In another embodiment, the choice of second therapeutic agent can be made from any second therapeutic agent known to be useful for co-administration with Compound 1. Examples of such agents and the conditions and diseases for which each may be used in conjunction with a compound of this invention include antiplatelet agents (e.g., aspirin and clopidgrel) in the treatment of stroke patients, and probucol.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich, et al., Cancer Chemother. Rep., 50: 219 (1966). Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 20 mg/day to about 400 mg/day. Administration can be in one or more doses per day (e.g., multiple doses). When multiple doses are used, the amount of each dose can be the same or different.

In a particular embodiment, an effective amount of a compound of this invention can range from about 20 mg/day to about 200 mg/day, from about 25 mg/day to about 200 mg/day, from about 30 mg/day to about 200 mg/day, from about 35 mg/day to about 200 mg/day, from about 40 mg/day to bout 200 mg/day, from about 45 mg/day to about 200 mg/day, from about 50 mg/day to about 200 mg/day. For example, an effective amount per day can be about 20 mg/day, 25 mg/day, 30 mg/day, or about 35 mg/day, or about 40 mg/day, or about 45 mg/day, or about 50 mg/day, or about 55 mg/day, or about 60 mg/day, or about 65 mg/day, or about 70 mg/day or about 75 mg/day, or about 80 mg/day, or about 85 mg/day, or about 90 mg/day, or about 95 mg/day, or about 100 mg/day, or about 150 mg/day, or about 200 mg/day.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells, et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

Some of the second therapeutic agents referenced above may act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

The invention also provides a method of treating a disease that is susceptible to treatment by an antagonist of the phosphodiesterase III comprising the step of administering to a patient in need thereof an effective amount of a compound of Formula (I) or a pharmaceutical composition of this invention comprising a compound of Formula (I) and a pharmaceutically acceptable carrier.

Diseases or conditions susceptible to treatment by inhibition of phosphodiesterase III include, but are not limited to: chronic arterial occlusive disease, diabetic mellitus complications (e.g., complication of peripheral), intermittent claudication, intimal proliferation, restenosis, intracranial arterial stenosis, recurrent strokes, cerebral infarction, cerebrovascular disorders, artherosclerosis, atherothrombosis complications, peripheral vascular disease, Reynaud's Disease, sexual dysfunction, ulcers, cerebral circulation impairment, thrombolytic disorders, inflammation, hypotension, asthma, ischemic heart disease, coronary heart disease and acute coronary syndrome.

In a particular embodiment, the method of the invention is used to treat chronic arterial occlusive disease, intermittent claudication or stroke in a patient in need thereof comprising administering to the patient an effective amount of a compound of Formula (I) or a pharmaceutical composition comprising a compound of Formula (I) and a pharmaceutically acceptable carrier.

In another particular embodiment, the method of the invention is used to treat a patient suffering from or susceptible to Type 2 diabetes or metabolic syndrome X.

Methods delineated herein also include those wherein the patient is identified as in need of a particular stated treatment. Identifying a patient in need of such treatment can be in the judgment of a patient or a health care professional and can be subjective (e.g., opinion) or objective (e.g., measurable by a test or diagnostic method).

In another embodiment, the above methods of treatment comprise the further step of co-administering to the patient one or more second therapeutic agents. The choice of second therapeutic agent may be made from one or more additional compounds of the invention, or any second therapeutic agent known to be useful for co-administration with cilostazol. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In one embodiment, the second therapeutic agent is selected from aspirin, clopidogrel or ao combination thereof, and the patient is suffering from or susceptible to stroke or has recently been implanted with a drug-eluting stent.

In another embodiment, the second therapeutic agent is probucol, and the patient is suffering from or susceptible to type 2 diabetes or metabolic syndrome X.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to the patient at another time during a course of treatment.

Effective amounts of these second therapeutic agents are well known to those skilled in the art and guidance for dosing may be found in patents and published patent applications referenced herein, as well as in Wells, et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a patient, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

When the compounds, pharmaceutically acceptable salts thereof, compositions and pharmaceutical compositions of this invention are co-administered with another antiplatelet agent (e.g., aspirin or clopidogrel), the patient benefit from reduction of platelet aggregation that leads to other disorders.

In yet another aspect, the invention provides a compound of Formula (I), a pharmaceutically acceptable salt thereof, or a pharmaceutical composition of Formula (I), alone or together with one or more of the above-described second therapeutic agents for treatment or prevention in a patient of a disease, disorder or symptom set forth above. In a particular embodiment the disease is stroke. In a more particular embodiment, the disease is stroke and the second agent is aspirin or clopidogrel.

In other aspects, the methods herein include those further comprising monitoring patient response to the treatment administrations. Such monitoring can include periodic sampling of patient tissue, fluids, specimens, cells, proteins, chemical markers, genetic materials, etc. as markers or indicators of the treatment regimen. In other methods, the patient is prescreened or identified as in need of such treatment by assessment for a relevant marker or indicator of suitability for such treatment.

In another embodiment, the invention provides a method of modulating the activity of phosphodiesterase III in a cell, comprising contacting a cell with one or more compounds of Formula (I), a pharmaceutically acceptable salt thereof, or pharmaceutical compositions of Formula (I) as described herein.

Diagnostic Methods and Kits

The compounds and compositions of this invention are also useful as reagents in methods for determining the concentration of cilostazol in solution or biological sample such as plasma, examining the metabolism of cilostazol and other analytical studies.

According to one embodiment, the invention provides a method of determining the concentration, in a solution or a biological sample, of cilostazol, comprising the steps of:

a) adding a known concentration of a compound of Formula I to the solution of biological sample;

b) subjecting the solution or biological sample to a measuring device that distinguishes cilostazol from a compound of Formula I;

c) calibrating the measuring device to correlate the detected quantity of the compound of Formula I with the known concentration of the compound of Formula I added to the biological sample or solution; and d) measuring the quantity of cilostazol in the biological sample with the calibrated measuring device; and e) determining the concentration of cilostazol in the solution of sample using the correlation between detected quantity and concentration obtained for a compound of Formula I.

Measuring devices that can distinguish cilostazol from the corresponding compound of Formula I include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a patient following administration of the compound of Formula I. This method comprises the steps of obtaining a serum, urine or feces sample from the patient at a period of time following the administration of the compound of Formula I to the patient; and comparing the amount of the compound of Formula I with the metabolic products of the compound of Formula I in the serum, urine or feces sample.

The present invention also provides kits for use to treat chronic arterial occlusive disease, diabetic mellitus complications (e.g., complication of peripheral vasuclature), intermittent claudication, intimal proliferation, restenosis, intracranial arterial stenosis, recurrent strokes, cerebral infarction, cerebrovascular disorders, arthrosclerosis, atherothrombosis complications, peripheral vascular disease, Reynaud's Disease, sexual dysfunction, ulcers, cerebral circulation impairment, thrombolytic disorders, inflammation, hypotension, asthma, ischemic heart disease, coronary heart disease and acute coronary syndrome.

These kits comprise (a) a pharmaceutical composition comprising a compound of Formula (I), a pharmaceutically acceptable thereof or a composition of Formula (I), wherein the pharmaceutical composition is in a container; and (b) instructions describing a method of using the pharmaceutical composition to treat chronic arterial occlusive disease, diabetic mellitus complications (e.g., complication of peripheral vasuclature), intermittent claudication, intimal proliferation, restenosis, intracranial arterial stenosis, recurrent strokes, cerebral infarction, cerebrovascular disorders, arthrosclerosis, atherothrombosis complications, peripheral vascular disease, Reynaud's Disease, sexual dysfunction, ulcers, cerebral circulation impairment, thrombolytic disorders, inflammation, hypotension, asthma, ischemic heart disease, coronary heart disease and acute coronary syndrome.

The container can be any vessel or other sealed or sealable apparatus that can hold the pharmaceutical composition. Examples include bottles, ampules, divided or multi-chambered holders bottles, wherein each division or chamber comprises a single dose of the composition, a divided foil packet wherein each division comprises a single dose of the composition, or a dispenser that dispenses single doses of the composition. The container can be in any conventional shape or form as known in the art which is made of a pharmaceutically acceptable material, for example, a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example, a conventional cardboard box would not generally be used to hold a liquid suspension. It is feasible that more than one container can be used together in a single package to market a single dosage form. For example, tablets may be contained in a bottle, which is in turn contained within a box. In on embodiment, the container is a blister pack.

The kit can additionally comprise a memory aid of the type containing information and/or instructions for the physician, pharmacist or patient. Such memory aids include numbers printed on each chamber or division containing a dosage that corresponds with the days of the regimen which the tablets or capsules so specified should be ingested, or days of the week printed on each chamber or division, or a card which contains the same type of information. For single dose dispensers, memory aids further include a mechanical counter which indicates the number of daily doses that have been dispensed and a battery-powered micro-chip memory coupled with a liquid crystal readout and/or audible reminder signal which, for example, reads out the date that the last daily dose has been taken and/or reminds one when the next dose is to be taken. Other memory aids useful in such kits are a calendar printed on a card, as well as other variations that will be readily apparent.

The kits of this invention can also comprise a device to administer or to measure out a unit dose of the pharmaceutical composition. Such device may include an inhaler if the composition is an inhalable composition; a syringe and needle if the composition is an injectable composition; a syringe, spoon, pump, or a vessel with or without volume markings if the composition is an oral liquid composition; or any other measuring or delivery device appropriate to the dosage formulation of the composition present in the kit.

Assays for assessing metabolic stability are well known in the art and are described, for example, in Obach, R. S., *Drug Metab Disp,* 27: 1350 (1999), "Prediction of human clearance of twenty-nine drugs from hepatic microsomal intrinsic clearance data: An examination of in vitro half-life approach and nonspecific binding to microsomes"; Houston, J. B., et al., *Drug Metab Rev,* 29: 891 (1997), "Prediction of hepatic clearance from microsomes, hepatocytes, and liver slices;" Houston, J. B., *Biochem Pharmacol,* 47: 1469 (1994), "Utility of in vitro drug metabolism data in predicting in vivo metabolic clearance"; Iwatsubo, T., et al., *Pharmacol Ther,* 73: 147 (1997), "Prediction of in vivo drug metabolism in the human liver from in vitro metabolism data"; and Lave, T., et al., *Pharm. Res,* 14: 152 (1997), "The use of human hepatocytes to select compounds based on their expected hepatic extraction ratios in humans."

Synthetic Procedures

The synthesis of compounds of Formula (I) can be readily achieved by synthetic chemists of ordinary skill. Relevant procedures are disclosed, for instance in: U.S. Pat. No. 4,277,479; International Publication Nos. WO2004/062571 and WO20042014283; Japanese Applications JP2005350474 and JP2004506043; and the Chinese Applications CN1002-2602 20051226 and CN1002-8804 20050815.

Additionally, similar chemistry can be found in Occhiato, Ernesto, G., et al. *Journal of Medicinal Chemistry* 47(14): 3546-3560 (2004) and in JP 2000229944A, Preparation of 6-hydroxy-2-oxo-1,2,3,4-tetrahydroquinoline, by Lee, Byon Suku; Park, In Kyu; Shin, Sun Fun, Jpn. Kokai Tokkyo Koho (2000).

Such methods can be carried out utilizing corresponding deuterated and optionally, other isotope-containing reagents to synthesize the compounds delineated herein, or invoking standard synthetic protocols known in the art for introducing isotopic atoms to a chemical structure.

A convenient method for synthesizing compounds of Formula (I) is depicted in the Scheme 1. Suitable methods for preparing intermediates useful in the synthesis of the compounds of Formula (I) are depicted in Schemes 2-3.

Synthetic Schemes and Procedures

Scheme 1:

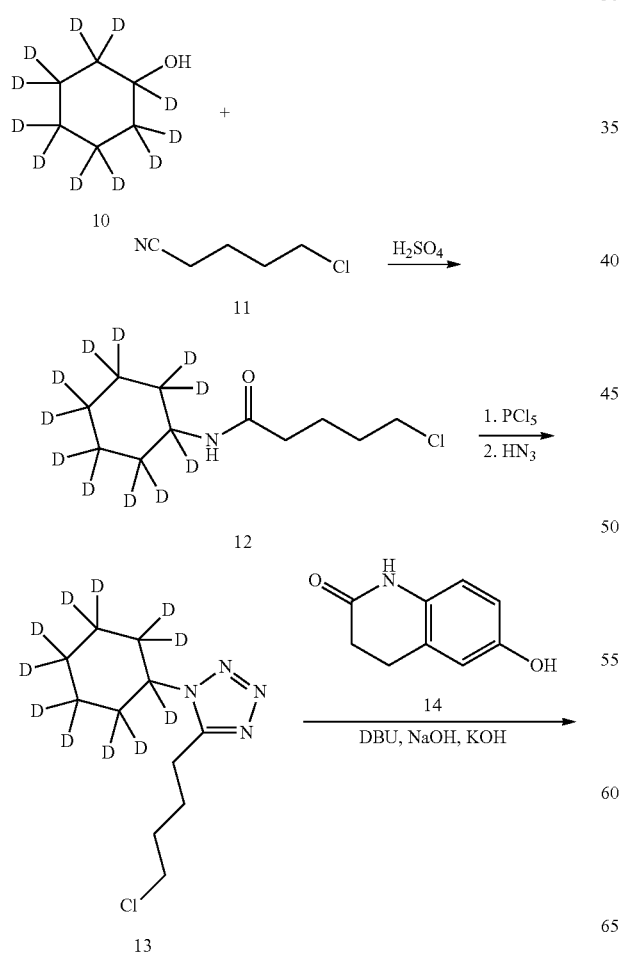

Scheme 2:

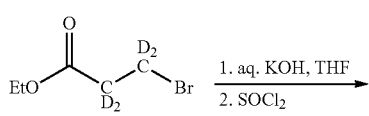

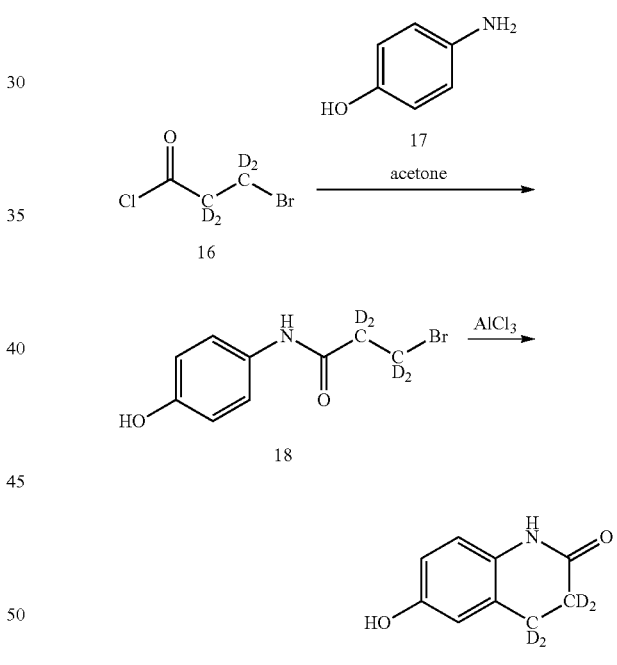

Scheme 3:

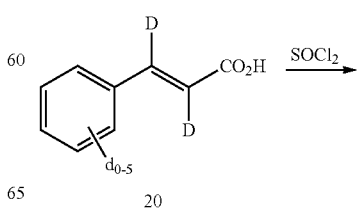

-continued

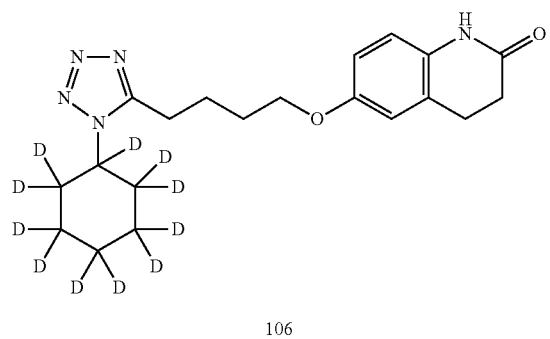

-continued

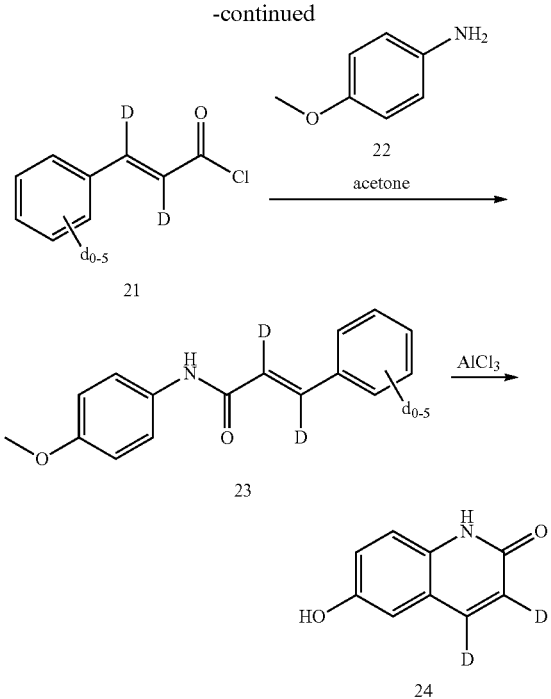

The compounds of interest may be prepared in the following way.

Deuterated reagents and/or deuterated intermediates can be used where appropriate in the provided synthetic routes to afford the compounds of interest. For example, as shown in Scheme 1 a deuterated alcohol such as commercially-available cyclohexan-d11-ol 10 is reacted with commercially-available 5-chlorovaleronitrile 11 (or appropriately-deuterated versions thereof) in the presence of sulfuric acid to yield amide 12. Treatment with phosphorus pentachloride, followed by cyclization with hydrazoic acid affords chloride 13. Alkylation of commercially-available 3,4-dihydro-6-hydroxy-2(1H)-quinolinone 14 in the presence of DBU, NaOH and KOH affords desired deuterated compounds such as 106.

Scheme 2 depicts the synthesis of deuterated lactam 19 which could be incorporated into the synthetic route of Scheme 1 to produce other desired deuterated compounds. As shown in Scheme 2, commercially-available ethyl 3-bromopropionate-2,2,3,3-d4 15 is hydrolyzed with aqueous KOH and is then converted to the acid chloride 16 via treatment with thionyl chloride. Acylation of commercially-available 4-aminophenol 17 affords amide 18. Friedel-Crafts reaction with aluminum trichloride provides desired deuterated lactam 19.

In yet another example, as shown in Scheme 3, deuterated lactam 24 could be produced from deuterated carboxylic acid 20 in a manner similar to that of Wang, T. C.; et al. Synthesis (1997), (1), 87-90, and then be incorporated into the synthetic route of Scheme 1 to produce other desired deuterated compounds.

Additional methods of synthesizing compounds of Formula (I) and their synthetic precursors, including those within routes not explicitly shown in schemes herein, are within the means of chemists of ordinary skill in the art. Methods for optimizing reaction conditions and, if necessary, minimizing competing by-products, are also known in the art. Reaction optimization and scale-up may advantageously utilize high-speed parallel synthesis equipment and computer-controlled microreactors (e.g., *Design And Optimization in Organic Synthesis,* 2nd Edition, Carlson, R., Ed, 2005; Elsevier Science Ltd.; Jähnisch, K., et al., Angew. *Chem. Int. Ed. Engl.* 2004, 43: 406; and references therein).

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Certain intermediates can be used with or without purification (e.g., filtration, distillation, sublimation, crystallization, trituration, solid phase extraction, and chromatography).

Combinations of substituents and variables envisioned by this invention are only those that result in the formation of stable compounds.

A description of example embodiments of the invention follows.

EXAMPLES

Example 1

Synthesis of 6-(4-(1-(cyclohexyl-d$_{11}$)-1H-tetrazol-5-yl) butoxy)-3,4-dihydroquinolin-2(1H)-one (106). Compound 106 was prepared according to Scheme 4 below.

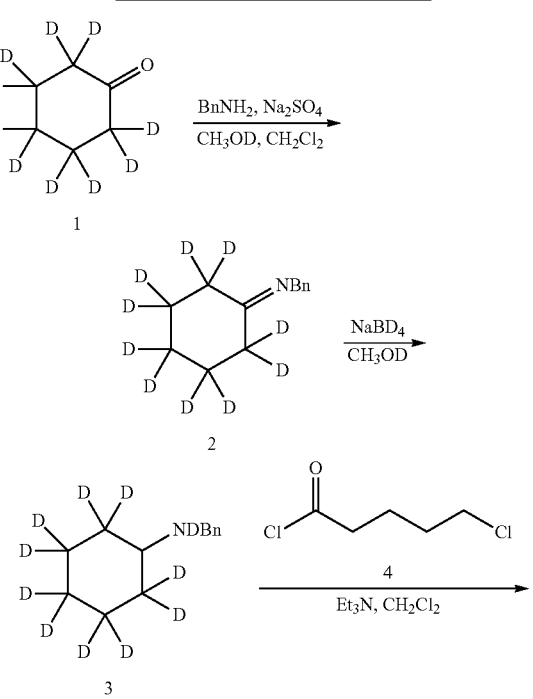

-continued

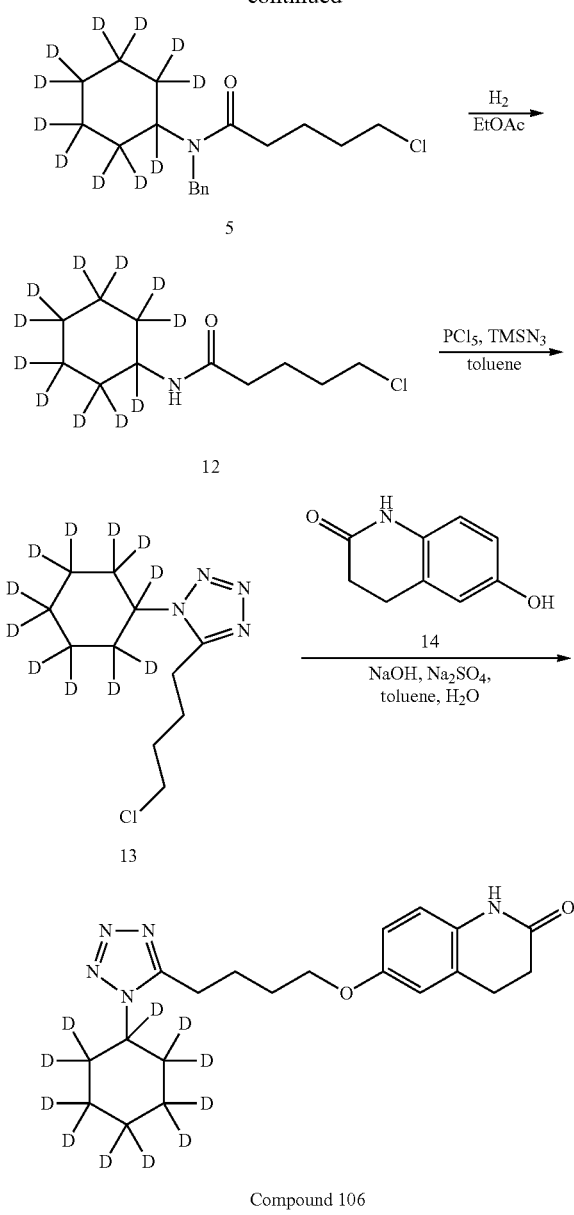

Compound 106

Synthesis of 6-(4-(1-(cyclohexyl-$d_{11}$)-1H-tetrazol-5-yl)butoxy)-3,4-dihydroquinolin-2(1H)-one (Compound 106). As depicted in Scheme 4 above, and in a similar manner to Compound 107 shown below, commercially-available cyclohexanone-d10 (1) was converted via a six-step sequence into desired Compound 106. HPLC (method: 20 mm C18-RP column—gradient method 2-95% ACN+0.1% formic acid in 3.3 min with 1.7 min hold at 95% ACN; Wavelength: 254 nm): retention time: 3.22 min. MS (M+H): 381.3.

Example 2

Synthesis of 6-(4-(1-(4,4-$d_2$-cyclohexyl)-1H-tetrazol-5-yl)butoxy)-3,4-dihydroquinolin-2(1H)-one (107). Compound 107 was prepared as outlined in Scheme 5 below. Details of the synthesis are set forth below.

Scheme 5. Preparation of Compound 107.

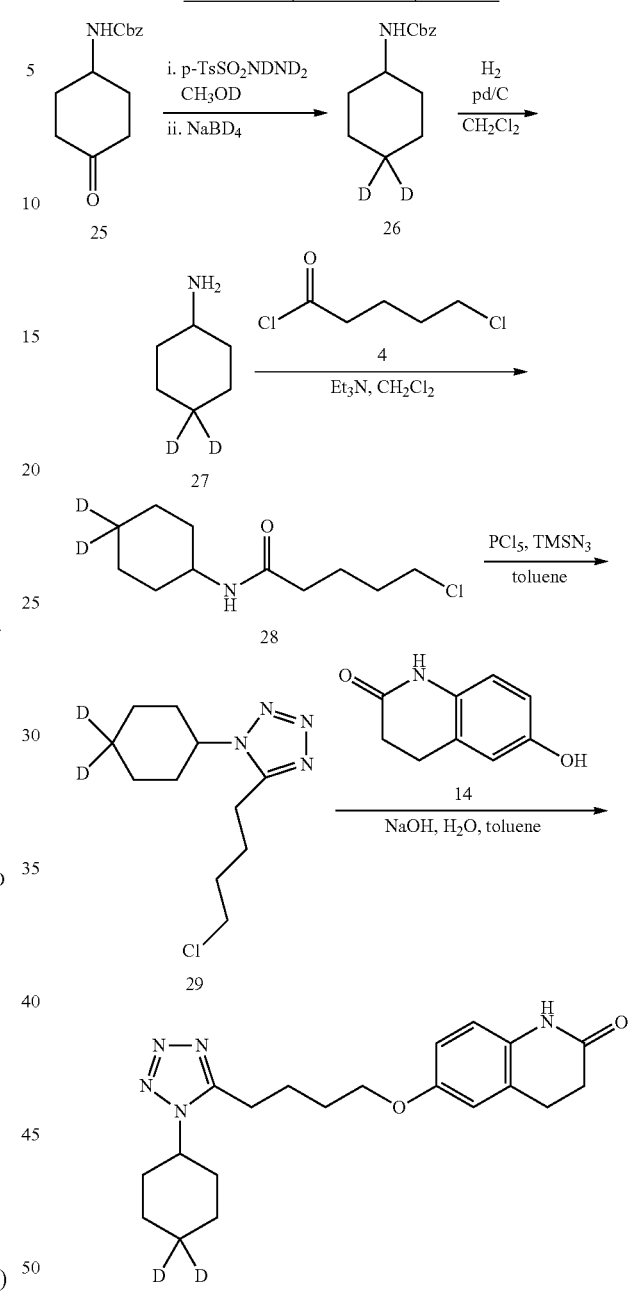

Compound 107

Synthesis of benzyl-(4,4-$d_2$-cyclohexyl)carbamate (26). N,N,N-$d_3$-(p-toluenesulfonyl)hydrazine (11.8 g, 63 mmol) was added to a solution of benzyl 4-oxocyclohexylcarbamate 25 (15 g, 63 mmol) in $CH_3OD$ (180 mL). The reaction mixture was stirred at room temperature for 1 h with a white solid precipitating. The mixture was cooled to 0° C., and sodium borodeuteride (11.4 g, 315 mmol) was added to the reaction mixture in portions. After gas evolution ceased, the reaction mixture was heated at reflux until a clear solution was obtained (0.5 h). The reaction mixture was cooled to room temperature and stirred overnight. The reaction mixture was concentrated under reduced pressure and water (1 L) and methylene chloride (500 mL) were added to the residue. The aqueous layer was separated and extracted with methylene chloride (3×300 mL). The combined organic phases were washed with brine (200 mL), dried over sodium sulfate (100 g) and concentrated under reduced pressure. The crude product was purified by chromatography on silica gel, eluting with heptanes/ethyl acetate (5:1), to give 12.5 g (88%) of benzyl (4,4-$d_2$-cyclohexyl)carbamate 26 as a white solid. $^1$H NMR (CDCl$_3$) δ: 7.38 (m, 5H), 5.08 (s, 1H), 4.62 (s, 1H), 3.53 (m, 1H), 1.92 (m, 2H), 1.71 (m, 2H), 1.32 (m, 2H), 1.14 (2H); MS (M+H): 236.3.

Synthesis of 4,4-$d_2$-cyclohexylamine (27). A mixture of benzyl (4,4-$d_2$-cyclohexyl)carbamate 26 (4 g, 17 mmol) in methylene chloride (60 mL) and 10% Pd—C (2 g) was hydrogenated (shaken) overnight at 3 Bar H$_2$ pressure. The mixture was filtered through Celite and the pad washed with methylene chloride (200 mL). The filtrate was concentrated by distillation at atmospheric pressure to give crude 4,4-$d_2$-cyclohexylamine 27 that was used directly for the next reaction.

Synthesis of 5-chloro-N-(4,4-$d_2$-cyclohexyl)pentanamide (28). A solution of crude 4,4-$d_2$-cyclohexylamine 27 (~16.8 mmol) and triethylamine (2.4 mL, 18.5 mmol) in methylene chloride (20 mL) was cooled in an ice-bath and 5-chlorovaleroyl chloride 4 (2 mL, 18.5 mmol) was added dropwise. The reaction mixture was allowed to warm to room temperature and was stirred overnight. The reaction mixture was diluted with methylene chloride (50 mL) and washed consecutively with saturated sodium bicarbonate solution, water, and brine. The organic solution was dried over sodium sulfate, filtered and concentrated under reduced pressure. The crude product was purified by column chromatography on silica gel, eluting with heptanes/ethyl acetate: (2:1 to 1:1) to give 650 mg (18% over 2 steps) of 5-chloro-N-(4,4-$d_2$-cyclohexyl)pentanamide 28. $^1$H NMR (CDCl$_3$) δ: 5.36 (s, 1H), 3.78 (m, 2H), 3.56 (t, 2H), 2.22 (t, 2H), 1.82 (m, 8H), 1.32 (m, 2H), 1.12 (m, 2H); MS (M+H): 220.1.

Synthesis of 5-(4-chlorobutyl)-1-(4,4-$d_2$-cyclohexyl)-1H-tetrazole (29). Phosphorous pentachloride (806 mg, 3.86 mmol) was added at room temperature to a solution of 5-chloro-N-(4,4-$d_2$-cyclohexyl)pentanamide 28 (650 mg, 2.97 mmol) in toluene (15 mL). After the reaction mixture was stirred for 3 h at room temperature, trimethylsilyl azide (0.57 mL, 4.3 mmol) was added. The reaction mixture was stirred at room temperature overnight. Water (15 ml) was added to the reaction mixture, the phases were separated, and the aqueous layer was extracted with toluene (3×15 mL). The combined organic phases were washed with brine, dried over sodium sulfate and concentrated under reduced pressure to give 640 mg (90%) of 29 as clear oil. $^1$H NMR (CDCl$_3$) δ: 4.18 (m, 1H), 3.61 (t, 2H), 2.92 (t, 2H), 2.00 (m, 10H), 1.43 (m, 2H). MS (M+H): 245.3.

Synthesis of 6-(4-(1-(4,4-$d_2$-cyclohexyl)-1H-tetrazol-5-yl)butoxy)-3,4-dihydroquinolin-2(1H)-one (Compound 107). To a mixture of 6-hydroxy-3,4-dihydroquinoline-2-one 14 (471 mg, 2.89 mmol) and sodium hydroxide (116 mg, 2.89 mmol) in water (10 mL) was added toluene (1.6 mL), 5-(4-chlorobutyl)-1-(4,4-$d_2$-cyclohexyl)-1H-tetrazole 29 (640 mg, 2.62 mmol), sodium sulfate (490 mg) and Aliquot® 336 (0.062 mL). The reaction mixture was heated at reflux for 2-3 days. The mixture was cooled to room temperature and diluted with water (20 mL) and toluene (20 mL). The aqueous phase was extracted with toluene (3×20 mL). The combined organic phases were washed with brine, dried over sodium sulfate and concentrated under reduced pressure. The crude product was purified by automated column chromatography on an Analogix system using 0-100% ethyl acetate/heptanes to give 220 mg of Compound 107 as a white solid. $^1$H NMR (CDCl$_3$) δ: 7.66 (m, 1) 6.68 (m, 3H), 4.18 (m, 1H), 3.98 (t, 2H), 2.92 (m, 4H), 2.61 (t, 2H), 2.00 (m, 10H), 1.39 (m, 2H). HPLC (method: 20 mm C18-RP column—gradient method 2-95% ACN+0.1% formic acid in 3.3 min with 1.7 min hold at 95% ACN; Wavelength: 254 nm): retention time: 3.22 min; 94% purity. MS (M+H): 372.3.

Biological Testing

Example 3

Determination of Metabolic Stability

This assay provides a method of determining the metabolic stability of the compounds described herein in pooled liver microsomal incubations. A method for conducting full scan LC-MS analysis for the detection of major metabolites is also provided.

Samples to be tested are exposed to pooled human, dog, and rat liver microsomes, and then analyzed using HPLC-MS (or MS/MS) detection. For determining metabolic stability, multiple reaction monitoring (MRM) is used to measure the disappearance of the sample. For metabolite detection, Q1 full scans are used as survey scans to detect the major metabolites.

Human and rat liver microsomes are obtained from Xenotech (Lenexa, Kans.). The incubation mixture is prepared as follows:

| Reaction Mixture Composition | |
| --- | --- |
| Liver Microsomes | 0.5-2.0 mg/mL |
| NADPH | 1 mM |
| Potassium Phosphate, pH 7.4 | 100 mM |
| Magnesium Chloride | 10 mM |
| Test Compound | 0.1-1 µM |

The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 0.1-1 µM. An aliquot of the reaction mixture is prepared as a blank control by the addition of plain organic solvent (not the test compound). The reaction is initiated by the addition of cofactors (not into the negative controls), and then incubated in a shaking water bath at 37° C. Aliquots (200 µL) are withdrawn in triplicate at 0, 15, 30, 60, and 120 minutes and combined with 800 µL of ice-cold 50/50 acetonitrile/dH$_2$O to terminate the reaction. The positive controls, testosterone and propranolol, are run simultaneously with the test compounds in separate reactions.

LC-MS-MS Analysis

All samples are analyzed using LC-MS (or MS/MS). An LC-MRM-MS/MS method is used for metabolic stability. Also, Q1 full scan LC-MS methods are performed on the blank matrix and the test compound incubation samples The Q1 scans serve as survey scans to identify any sample unique peaks that might represent the possible metabolites. The masses of these potential metabolites can be determined from the Q1 scans.

Results: Metabolic Stability

The percents remaining of the test compounds in human and/or rat liver microsomes are summarized. The positive control (testosterone and propranolol) metabolism data are also summarized and include results from the assay performed with incubation of the test compounds. The natural log of the percent remaining is plotted versus time. A linear fit is used to determine the rate constant. The elimination half-lives associated with the disappearance of the test and control compounds are determined and their relative metabolic stability compared.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:
1. A compound selected from:

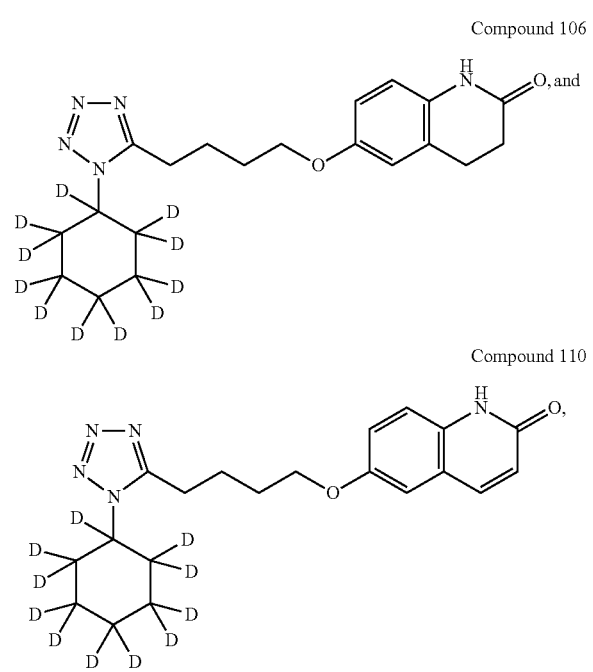

or a pharmaceutically acceptable salt of either of the foregoing, wherein each compound or pharmaceutically acceptable salt thereof has an isotopic enrichment factor for each indicated deuterium atom of at least 3000 and wherein for each compound or pharmaceutically acceptable salt thereof any atom not designated as deuterium is present at its natural isotopic abundance.

2. A composition suitable for pharmaceutical use comprising a compound of claim 1 and a pharmaceutically acceptable carrier.

3. The composition of claim 2, further comprising a second therapeutic agent useful in treating a patient suffering from or susceptible to arterial occlusive disease, intermittent claudication or stroke.

4. The composition of claim 3, wherein the second therapeutic agent is selected from aspirin, clopidogrel and probucol.

5. A method of treating a disease selected from chronic arterial occlusive disease, intermittent claudication, or stroke, in a patient in need thereof, comprising the steps of administering to the patient a pharmaceutically acceptable composition comprising:
a) a compound selected from:

or a pharmaceutically acceptable salt thereof; and
b) a pharmaceutically acceptable carrier,
wherein for each compound or pharmaceutically acceptable salt thereof any atom not designated as deuterium is present at its natural isotopic abundance.

6. The method of claim 5, further comprising co-administering to the patient in need thereof a second therapeutic agent useful in treating arterial occlusive disease, intermittent claudication or stroke.

7. The method of claim 6, wherein the second therapeutic agent is selected from aspirin and clopidogrel.

8. The compound of claim 1, wherein the isotopic enrichment factor for each indicated deuterium atom is at least 3500 (52.5% deuterium incorporation).

9. The compound of claim 1, wherein the isotopic enrichment factor for each indicated deuterium atom is at least 4000 (60% deuterium incorporation).

10. The compound of claim 1, wherein the isotopic enrichment factor for each indicated deuterium atom is at least 4500 (67.5% deuterium incorporation).

11. The compound of claim 1, wherein the isotopic enrichment factor for each indicated deuterium atom is at least 5000 (75% deuterium).

12. The compound of claim 1, wherein the isotopic enrichment factor for each indicated deuterium atom is at least 5500 (82.5% deuterium incorporation).

13. The compound of claim 1, wherein the isotopic enrichment factor for each indicated deuterium atom is at least 6000 (90% deuterium incorporation).

14. The compound of claim 1, wherein the isotopic enrichment factor for each indicated deuterium atom is at least 6333.3 (95% deuterium incorporation).

* * * * *